United States Patent [19]

Wade et al.

[11] 4,024,151

[45] May 17, 1977

[54] 4-PHENYLPIPERIDINYL (AND 4-PHENYL-TETRAHYDROPYRIDINYL) ALKYLAMINO-OXOALKANOIC ACIDS

[75] Inventors: Peter C. Wade, Pennington, N.J.; B. Richard Vogt, Yardley, Pa.

[73] Assignee: E. R. Squibb & Sons, Inc., Princeton, N.J.

[22] Filed: Sept. 29, 1975

[21] Appl. No.: 617,335

[52] U.S. Cl. .................. 260/295 AM; 260/293.73; 260/293.75; 260/293.76; 260/294.8 G; 260/294.9; 424/263; 424/267

[51] Int. Cl.² .............. C07D 211/70; C07D 211/16

[58] Field of Search ............... 260/294.8 G, 294.9, 260/295 AM

[56] References Cited

UNITED STATES PATENTS

| | | | |
|---|---|---|---|
| 3,864,493 | 2/1975 | Cairns et al. | 424/283 |
| 3,879,544 | 4/1975 | Reisner et al. | 424/337 |
| 3,883,653 | 5/1975 | Barth | 424/251 |
| 3,885,038 | 5/1975 | Pfister et al. | 424/283 |
| 3,927,006 | 12/1975 | Edenhofer | 260/294.8 G |
| 3,951,987 | 4/1976 | Edenhofer | 260/295 AM |

FOREIGN PATENTS OR APPLICATIONS 1,154,260   6/1969   United Kingdom ........ 260/295 AM

OTHER PUBLICATIONS

Physicians Desk Reference, (PDR), 1974, pp. 760–761.

*Primary Examiner*—Norman A. Drezin
*Attorney, Agent, or Firm*—Lawrence S. Levinson; Merle J. Smith; Donald J. Barrack

[57] ABSTRACT

Compounds having the formula

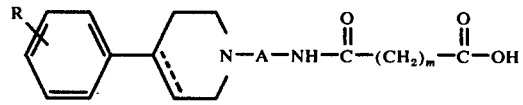

wherein A is a straight or branched chain alkylene group; R is hydrogen, halogen, alkyl, alkoxy, alkylthio, trifluoromethyl, nitro, amino, or cyano; and m is 2, 3 or 4; are useful in the treatment of allergic conditions in mammals.

4 Claims, No Drawings

4-PHENYLPIPERIDINYL (AND 4-PHENYL-TETRAHYDROPYRIDINYL) ALKYLAMINO-OXOALKANOIC ACIDS

SUMMARY OF THE INVENTION

Useful pharmaceutical activity is exhibited by compounds having the formula

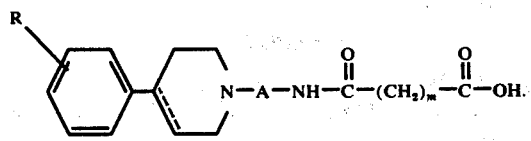

In formula I, and throughout the specification, the symbols are as defined below.

R can be hydrogen, halogen, alkyl, alkoxy, alkylthio, trifluoromethyl, nitro, amino, or cyano;

A can be a straight or branched chain alkylene group having 2 to 8 carbon atoms; and $m$ can be 2, 3, or 4.

The broken line in the piperidine nucleus represents the optional presence of ethylenic unsaturation.

The term "alkyl," as used throughout the specification, refers to alkyl groups having 1 to 4 carbon atoms.

The term "alkoxy," as used throughout the specification, refers to groups having the formula Y-O- wherein Y is alkyl as defined above.

The term "alkylthio," as used throughout the specification, refers to groups having the formula Y-S- wherein Y is alkyl as defined above.

The term "halogen," as used throughout the specification, refers to fluorine, chlorine, bromine, and iodine; fluorine, chlorine, and bromine are the preferred halogens.

DETAILED DESCRIPTION OF THE INVENTION

The compounds of formula I, and their pharmaceutically acceptable salts, are useful in treating various allergic conditions in mammalian species such as mice, cats, dogs, etc., when administered in amounts ranging from about 1 milligram to about 500 milligrams per kilogram of body weight per day. The compounds can be used prophylactically or therapeutically to treat various allergic and immunological disorders and in particular to treat certain types of asthma, hay-fever, and rhinitis. A preferred dosage regimen would be from about 3 milligrams to about 200 milligrams per kilogram of body weight per day administered in a single dose or plurality of divided doses.

The compounds of formula I, and the pharmaceutically acceptable salts thereof, are anti-allergics which inhibit the effects of certain antigen-antibody reactions and in particular inhibit the release of mediators such as histamine. The antiallergy activity of these compounds is determined by the reaginic antibody induced passive cutaneous anaphylaxis (PCA) reaction in rats. (See Bach, Immediate Hypersensitivity: Laboratory Models and Experimental Findings, Ann. Rep. Med. Chem., 7: 238-248 (1972), for a discussion of the pedictability of clinical efficacy of compounds active in the PCA).

A compound of formula I, or a salt thereof, can be administered by the inhalation of an aerosol or powder as described in U.S. Pat. No. 3,772,336 (i.e., breathing finely divided particles of the active ingredient into the lungs), orally, or parenterally. Powders can be prepared by comminuting the active ingredient with a similarly comminuted diluent such as starch or lactose. Suitable forms for oral administration include capsules, tablets, and syrups, and a suitable form for parenteral administration is a sterile injectable. Such unit dosage forms are prepared by compounding with a conventional vehicles, excipients, binders, preservatives, stabilizers, flavoring agents or the like as called for by acceptable pharmaceutical practice. Also, the compounds of this invention can be formulated with other pharmaceutically active compounds such as bronchodilators, steroids, antihistamines, etc.

The products of formula I can be prepared using as starting materials compounds having the formulas

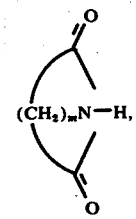

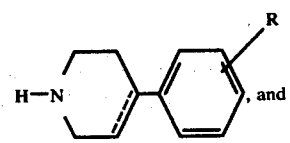

X' — A — X   IV.

In formula IV, and throughout the specification, the symbols X and X' can be the same or different and can be halogen (preferably chlorine or bromine), alkylsulfonate (e.g., methanesulfonate), or arylsulfonate (e.g., toluenesulfonate).

Reaction of a compound of formula II with a compound of formula IV yields an intermediate having the formula

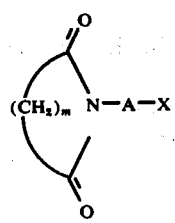

The reaction can be run in a polar organic solvent, e.g., dimethylsulfoxide or dimethylformamide, in the presence of alkali.

Reaction of an intermediate of formula V with a pyridine derivative of formula III yields an intermediate having the formula

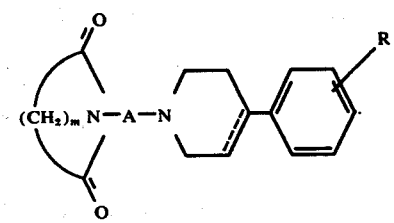

The reaction can be run in an organic solvent, e.g., benzene, toluene, etc., preferably in the presence of an organic or inorganic base, e.g., a tertiary amine such as ethyldiisopropylamine or an alkali metal carbonate such as sodium carbonate. While reaction conditions are not critical, the reaction will most conveniently be run at the reflux temperature of the solvent.

An intermediate of formula VI can be converted to the corresponding product of formula I via acid hydrolysis. This is most conveniently carried out by extracting the reaction product of an intermediate of formula V and a pyridine derivative of formula III with a mineral acid (hydrochloric acid is preferred) and allowing the acid solution to stand for about 1 week. The hydrolysis can be accelerated by heating.

Other procedures for preparing the compounds of formula I are available. For example, an intermediate of formula VI can be prepared by first reacting a compound of formula II with an appropriate base, e.g., potassium hydroxide or thallous ethoxide. The resultant salt is reacted with a compound having the formula

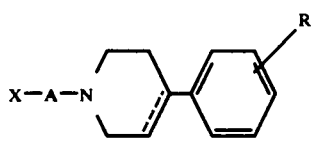

to yield an intermediate of formula VI. The compounds of formula I can then be prepared by acid hydrolysis as described above.

In still another method for preparing the compounds of formula I, a compound having the formula

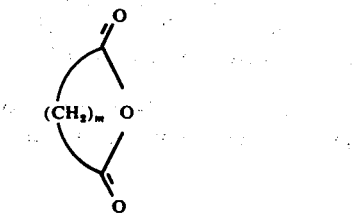

is reacted with a compound having the formula

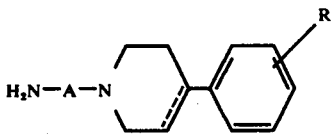

to yield the products of formula I directly.

The compounds of formula I can be converted into their pharmaceutically acceptable salts using procedures well known in the art. Acid addition salts such as the hydrohalides, nitrate, phosphate, sulfate, tartrate, maleate, fumarate, citrate, succinate, methanesulfonate, benzenesulfonate, toluenesulfonate, and the like, are specifically contemplated. Basic salts are also specifically contemplated. The compounds of formula I form salts with bases such as alkali metal hydroxides, sodium hydroxide, potassium hydroxide, etc.), alkaline earth metal hydroxides (e.g., calcium hydroxide, magnesium hydroxide, etc.), alkali metal carbonates (e.g., sodium carbonate, etc.) and alkali metal bicarbonates (e.g., potassium bicarbonate, etc.).

The following examples are specific embodiments of this invention.

EXAMPLE 1

5-[[4-(3,6-Dihydro-4-Phenyl-1(2H)-Pyridinyl)Butyl]Amino]-5-Oxopentanoic Acid, Hydrochloride (1:1)

A. N-(4-Bromobutyl)glutarimide

Sodium (5g) is dissolved in 100 ml of absolute ethanol and the sodium ethoxide solution is added to a solution of 23 g of glutarimide in 160 ml of warm absolute ethanol. The mixture is allowed to cool to 25° C with stirring and the solvent is removed under vacuum. To the residue is added 70 ml of dimethylformamide and 60 ml of 1,4-dibromobutane and the mixture is refluxed for 10 minutes. The solvent is removed under vacuum and the residue is shaken with hexane to remove excess 1,4-dibromobutane. The hexane layer is decanted off, the residue is taken up in ether and the insoluble material is filtered off. The ethereal filtrate is washed with 10% sodium hydroxide, 10% hydrochloric acid, water, and dried over sodium sulfate. The solvent is removed under vacuum to yield 26 g of N-(4-bromobutyl)glutarimide.

B. 5-[[4-(3,6-Dihydro-4-phenyl-1(2H)-pyridinyl)butyl]amino]-5-oxopentanoic acid, hydrochloride (1:1)

4-Phenyl-1,2,3,6-tetrahydropyridine hydrochloride (10 g) is converted to its free base and combined with 11.0 g of N-(4-bromobutyl)glutarimide and 18 g of sodium carbonate in 200 ml of toluene. The mixture is refluxed for 5 hours, cooled to 25°C and 50 ml of water is added. After stirring for 15 minutes, the layers are separated and the organic layer is filtered through fritted glass to remove insoluble material and then extracted with 10% hydrochloric acid. The acid solution is allowed to stand in an open beaker for 1 week during which time the product precipitates out. It is filtered off and dried at 70° C, 0.1 mm of Hg, for 12 hours to yield 6.3 g of the title compound, melting point 163°–165°C.

EXAMPLES 2–55

Following the procedure of Example 1, but substituting the compound listed in Column I for glutarimide, the compound listed in Column II for 1,4-dibromobutane and the compound listed in Column III for 4-phenyl-1,2,3,6-tetrahydropyridine hydrochloride, yields the compound listed in Column IV.

| Example | Column I | Column II | Column III | Column IV |
| --- | --- | --- | --- | --- |
| 2 | glutarimide | 1,2-dibromoethane | 4-(4-chlorophenyl)1,2,3,6-tetrahydropyridine | 5-[[2-[3,6-dihydro-4-(4-chlorophenyl)-1(2H)-pyridinyl]ethyl]amino]-5-oxopentanoic acid, hydrochloride |
| 3 | glutarimide | 1,3-dibromopropane | 4-(4-bromophenyl)-1,2,3,6-tetrahydropyridine | 5-[[3-[3,6-dihydro-4-(4-bromophenyl)-1(2H)-pyridinyl]propyl]amino]-5-oxopentanoic acid, hydrochloride |
| 4 | glutarimide | 1,5-dibromopentane | 4-(2-methylphenyl)-1,2,3,6-tetrahydropyridine | 5-[[5-[3,6-dihydro-4-(2-methylphenyl)-1(2H)-py- |

-continued

| Example | Column I | Column II | Column III | Column IV |
|---|---|---|---|---|
| | | | | ridinyl]pentyl]amino]-5-oxopentanoic acid, hydrochloride |
| 5 | glutarimide | 1,5-dibromohexane | 4-(3-methoxyphenyl)-1,2,3,6-tetrahydropyridine | 5-[[6-[3,6-dihydro-4-(3-methoxyphenyl)-1(2H)-pyridinyl]hexyl]amino]-5-oxopentanoic acid, hydrochloride |
| 6 | glutarimide | 1,7-dibromoheptane | 4-(4-methylthiophenyl)-1,2,3,6-tetrahydropyridine | 5-[[7-[3,6-dihydro-4-(4-methylthiophenyl)-1(2H)-pyridinyl]heptyl]amino]-5-oxopentanoic acid, hydrochloride |
| 7 | glutarimide | 1,8-dibromooctane | 4-(4-trifluoromethylphenyl)-1,2,3,6-tetrahydropyridine | 5-[[8-[3,6-dihydro-4-(4-trifluoromethylphenyl)-1(2H)-pyridinyl]octyl]amino]-5-oxopentanoic acid, hydrochloride |
| 8 | glutarimide | 1,3-dibromo-2-methylpropane | 4-(3-nitrophenyl)-1,2,3,6-tetrahydropyridine | 5-[[3-[3,6-dihydro-4-(3-nitrophenyl)-1(2H)-pyridinyl]-2-methylpropyl]amino]-5-oxopentanoic acid, hydrochloride |
| 9 | glutarimide | 1,2-dibromoethane | 4-(2-aminophenyl)-1,2,3,6-tetrahydropyridine | 5-[[2-[3,6-dihydro-4-(2-aminophenyl)-1(2H)-pyridinyl]ethyl]amino]-5-oxopentanoic acid, hydrochloride |
| 10 | glutarimide | 1,3-dibromopropane | 4-(2-cyanophenyl)-1,2,3,6-tetrahydropyridine | 5-[[3-[3,6-dihydro-4-(2-cyanophenyl)-1(2H)-pyridinyl]propyl]amino]-5-oxopentanoic acid, hydrochloride |
| 11 | succinimide | 1,2-dibromoethane | 4-phenyl-1,2,3,6-tetrahydropyridine | 4-[[2-(3,6-dihydro-4-phenyl-1(2H)-pyridinyl)-ethyl]amino]-4-oxobutanoic acid, hydrochloride |
| 12 | succinimide | 1,8-dibromooctane | 4-(2-chlorophenyl)-1,2,3,6-tetrahydropyridine | 4-[[8-[3,6-dihydro-4-(2-chlorophenyl)-1(2H)-pyridinyl]octyl]amino]-4-oxobutanoic acid, hydrochloride |
| 13 | succinimide | 1,3-dibromopropane | 4-(2-ethylphenyl)-1,2,3,6-tetrahydropyridine | 4-[[3-[3,6-dihydro-4-(2-ethylphenyl-1(2H)-pyridinyl]propyl]amino]-4-oxobutanoic acid, hydrochloride |
| 14 | succinimide | 1,4-dibromobutane | 4-(2-ethoxyphenyl)-1,2,3,6-tetrahydropyridine | 4-[[4-[3,6-dihydro-4-(2-ethoxyphenyl)-1(2H)-pyridinyl]butyl]amino]-4-oxobutanoic acid, hydrochloride |
| 15 | succinimide | 1,5-dibromopentane | 4-(2-ethylthiophenyl)-1,2,3,6-tetrahydropyridine | 4-[[5-[3,6-dihydro-4-(2-ethylthiophenyl)-1(2H)-pyridinyl]pentyl]amino]-4-oxobutanoic acid, hydrochloride |
| 16 | succinimide | 1,6-dibromohexane | 4-(3-trifluoromethylphenyl)-1,2,3,6-tetrahydropyridine | 4-[[6-[3,6-dihydro-4-(3-trifluoromethylphenyl)-1(2H)-pyridinyl]hexyl]amino]-4-oxobutanoic acid, hydrochloride |
| 17 | succinimide | 1,7-dibromoheptane | 4-(4-nitrophenyl)-1,2,3,6-tetrahydropyridine | 4-[[7-[3,6-dihydro-4-(4-nitrophenyl)-1(2H)-pyridinyl]heptyl]amino]-4-oxobutanoic acid, hydrochloride |
| 18 | succinimide | 1,2-dibromoethane | 4-(4-aminophenyl)-1,2,3,6-tetrahydropyridine | 4-[[2-[3,6-dihydro-4-(4-aminophenyl)-1(2H)-pyridinyl]ethyl]amino]-4-oxobutanoic acid, hydrochloride |
| 19 | succinimide | 1,5-dibromo-3-methylpentane | 4-(4-cyanophenyl)-1,2,3,6-tetrahydropyridine | 4-[[5-[3,6-dihydro-4-(4-cyanophenyl)-1(2H)-pyridinyl]3-methylpentyl]amino]-4-oxobutanoic acid, hydrochloride |
| 20 | adipimide | 1,2-dibromoethane | 4-phenyl-1,2,3,6-tetrahydropyridine | 6-[[2-(3,6-dihydro-4-phenyl-1(2H)-pyridinyl)-ethyl]amino]-6-oxohexanoic acid, hydrochloride |
| 21 | adipimide | 1,3-dibromopropane | 4-(3-fluorophenyl)-1,2,3,6-tetrahydropyridine | 6-[[3-[3,6-dihydro-4-(3-fluorophenyl)-1(2H)-pyridinyl]propyl]amino]-6-oxohexanoic acid, hydrochloride |
| 22 | adipimide | 1,3-dibromopropane | 4-(3-t-butylphenyl)-1,2,3,6-tetrahydropyridine | 6-[[3-[3,6-dihydro-4-(3-t-butylphenyl)-1(2H)-pyridinyl]propyl]amino]-6-oxohexanoic acid, hydrochloride |

-continued

| Example | Column I | Column II | Column III | Column IV |
|---|---|---|---|---|
| 23 | adipimide | 1,4-dibromobutane | 4-(2-ethoxyphenyl)-1,2-3,6-tetrahydropyridine | 6-[[4-[3,6-dihydro-4-(2-ethoxyphenyl)-1(2H)-pyridinyl]butyl]amino]-6-oxo-4-oxohexanoic acid, hydrochloride |
| 24 | adipimide | 1,5-dibromopentane | 4-(4-ethylthiophenyl)-1,2,3,6-tetrahydropyridine | 6-[[5-[3,6-dihydro-4-(4-ethylthiophenyl)-1(2H)-pyridinyl]pentyl]amino]-4-oxohexanoic acid, hydrochloride |
| 25 | adipimide | 1,6-dibromohexane | 4-(3-trifluoromethylphenyl)-1,2,3,6-tetrahydropyridine | 6-[[6-[3,6-dihydro-4-(3-trifluoromethylphenyl)-1(2H)-pyridinyl]hexyl]amino]-4-oxohexanoic acid, hydrochloride |
| 26 | adipimide | 1,7-dibromoheptane | 4-(3-nitrophenyl)-1,2,3,6-tetrahydropyridine | 6-[[7-[3,6-dihydro-4-(3-nitrophenyl)-1(2H)-pyridinyl]heptyl]amino]-4-oxohexanoic acid, hydrochloride |
| 27 | adipimide | 1,8-dibromooctane | 4-(3-aminophenyl)-1,2,3,6-tetrahydropyridine | 6-[[8-[3,6-dihydro-4-(3-aminophenyl)-1(2H)-pyridinyl]octyl]amino]-4-oxohexanoic acid, hydrochloride |
| 28 | adipimide | 1,2-dibromoethane | 4-(3-cyanophenyl)-1,2,3,6-tetrahydropyridine | 6-[[2-[3,6-dihydro-4-(3-cyanophenyl)-1(2H)-pyridinyl]ethyl]amino]-4-oxohexanoic acid, hydrochloride |
| 29 | glutarimide | 1,2-dibromoethane | 4-(4-chlorophenyl)piperidine | 5-[[2-[4-(4-chlorophenyl)piperidinyl]ethyl]amino]-5-oxopentanoic acid, hydrochloride |
| 30 | glutarimide | 1,3-dibromopropane | 4-(4-bromophenyl)piperidine | 5-[[3-[4-(4-bromophenyl)piperidinyl]propyl]amino]-5-oxopentanoic acid, hydrochloride |
| 31 | glutarimide | 1,5-dibromopentane | 4-(2-methylphenyl)piperidine | 5-[[5-[4-(2-methylphenyl)piperidinyl]pentyl]amino]-5-oxopentanoic acid, hydrochloride |
| 32 | glutarimide | 1,6-dibromohexane | 4-(3-methoxyphenyl)piperidine | 5-[[6-[4-(3-methoxyphenyl)piperidinyl]hexyl]amino]-5-oxopentanoic acid, hydrochloride |
| 33 | glutarimide | 1,7-dibromoheptane | 4-(4-methylthiophenyl)piperidine | 5-[[7-[4-(4-methylthiophenyl)piperidinyl]heptyl]amino]-5-oxopentanoic acid, hydrochloride |
| 34 | glutarimide | 1,8-dibromooctane | 4-(3-trifluoromethylphenyl)piperidine | 5-[[8-[4-(3-trifluoromethylphenyl)piperidinyl]octyl]amino]-5-oxopentanoic acid, hydrochloride |
| 35 | glutarimide | 1,3-dibromo-2-methylpropane | 4-(3-nitrophenyl)piperidine | 5-[[3-[4-(3-nitrophenyl)piperidinyl]-2-methylpropyl]amino]-5-oxopentanoic acid, hydrochloride |
| 36 | glutarimide | 1,2-dibromoethane | 4-(2-aminophenyl)piperidine | 5-[[2-[4-(2-aminophenyl)piperidinyl]ethyl]amino]-5-oxopentanoic acid, hydrochloride |
| 37 | glutarimide | 1,3-dibromopropane | 4-(2-cyanophenyl)piperidine | 5-[[3-[4-(2-cyanophenyl)piperidinyl]propyl]amino]-5-oxopentanoic acid, hydrochloride |
| 38 | succinimide | 1,2-dibromoethane | 4-phenylpiperidine | 4-[[2-(4-phenylpiperidinyl)ethyl]amino]-4-oxobutanoic acid, hydrochloride |
| 39 | succinimide | 1,8-dibromooctane | 4-(2-chlorophenyl)piperidine | 4-[[8-[4-(2-chlorophenyl)piperidinyl]octyl]amino]-4-oxobutanoic acid, hydrochloride |
| 40 | succinimide | 1,3-dibromopropane | 4-(2-ethylphenyl)piperidine | 4-[[3-[4-(2-ethylphenyl)piperidinyl]propyl]amino]-4-oxobutanoic acid |
| 41 | succinimide | 1,4-dibromobutane | 4-(2-ethoxyphenyl)-piperidine | 4-[[4-[4-(2-ethoxyphenyl)piperidinyl]butyl]amino]-4-oxobutanoic acid |
| 42 | succinimide | 1,5-dibromopentane | 4-(2-ethylthiophenyl)piperidine | 4-[[5-[4-(2-ethylthiophenyl)piperidinyl]pentyl]amino]-4-oxobutanoic acid |
| 43 | succinimide | 1,6-dibromohexane | 4-(3-trifluoromethylphenyl)piperidine | 4-[[6-[4-(3-trifluoromethylphenyl)piperidinyl]hexyl]amino]-4-oxobutanoic acid |

-continued

| Example | Column I | Column II | Column III | Column IV |
|---|---|---|---|---|
| 44 | succinimide | 1,7-dibromoheptane | 4-(4-nitrophenyl)piperidine | 4-[( 7-[4-(4-nitrophenyl)-piperidinyl]heptyl]amino]-4-oxobutanoic acid |
| 45 | succinimide | 1,2-dibromoethane | 4-(4-aminophenyl)piperidine | 4-[[2-[4-(4-aminophenyl)-piperidinyl]ethyl]amino]-4-oxobutanoic acid |
| 46 | succinimide | 1,5-dibromo-3-methylpentane | 4-(4-aminophenyl)piperidine | 4-[[5-[4-(4-aminophenyl)-piperidinyl]-3-methyl-pentyl]amino]-4-oxobutanoic acid |
| 47 | adipimide | 1,2-dibromoethane | 4-phenylpiperidine | 6-[[2-(4-phenylpiperidinyl)ethyl]amino]-6-oxohexanoic acid, hydrochloride |
| 48 | adipimide | 1,3-dibromopropane | 4-(4-fluorophenyl)piperidine | 6-[[3-[4-(4-fluorophenyl)-piperidinyl]propyl]amino]-6-oxohexanoic acid, hydrochloride |
| 49 | adipimide | 1,3-dibromopropane | 4-(4-t-butylphenyl)piperidine | 6-[( 3-[4-(4-t-butylphenyl)-piperidinyl]propyl]amino]-6-oxohexanoic acid, hydrochloride |
| 50 | adipimide | 1,4-dibromobutane | 4-(3-ethoxyphenyl)piperidine | 6-[[4-[4-(3-ethoxyphenyl)-piperidinyl]butyl]amino]-6-oxohexanoic acid, hydrochloride |
| 51 | adipimide | 1,5-dibromopentane | 4-(4-ethylthiophenyl)piperidine | 6-[[5-[4-(4-ethylthiophenyl)piperidinyl]pentyl]amino]-6-oxohexanoic acid, hydrochloride |
| 52 | adipimide | 1,6-dibromohexane | 4-(4-trifluoromethylphenyl)piperidine | 6-[[6-[4-(4-trifluoromethylphenyl)piperidinyl]-hexyl]amino]-6-oxohexanoic acid, hydrochloride |
| 53 | adipimide | 1,7-dibromoheptane | 4-(3-nitrophenyl)piperidine | 6-[[7-[4-(3-nitrophenyl)-piperidinyl]heptyl]amino]-6-oxohexanoic acid, hydrochloride |
| 54 | adipimide | 1,8-dibromooctane | 4-(3-aminophenyl)piperidine | 6-[[8-[4-(3-aminophenyl)-piperidinyl]octyl]amino]-6-hexanoic acid, hydrochloride |
| 55 | adipimide | 1,2-dibromoethane | 4-(3-cyanophenyl)piperidine | 6-[[2-[4-(3-cyanophenyl)-piperidinyl]ethyl]amino]-6-oxohexanoic acid, hydrochloride |

What is claimed is:

1. A compound having the formula

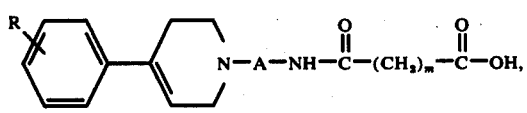

or a pharmaceutically acceptable salt thereof, wherein A is a straight or branched chain alkylene group having 2 to 8 carbon atoms, R is hydrogen, halogen, alkyl, alkoxy, alkylthio, trifluoromethyl, nitro, amino, or cyano; and $m$ is 2, 3, or 4; wherein the terms alkyl, alkoxy and alkylthio refer to groups having 1 to 4 carbon atoms.

2. A compound in accordance with claim 1 wherein A is an alkylene group having 2, 3, or 4 carbon atoms.

3. A compound in accordance with claim 1 where R is hydrogen.

4. The compound in accordance with claim 1 having the name 5-[[4-(3,6-dihydro-4-phenyl-1(2H)-pyridinyl)butyl]amino]-5-oxopentanoic acid, monohydrochloride.

* * * * *